United States Patent [19]
Wadley

[11] Patent Number: 5,556,065
[45] Date of Patent: Sep. 17, 1996

[54] INTENSIVE CARE EQUIPMENT CARRIAGE

[76] Inventor: Robert D. Wadley, 20 S. Sprague, Coldwater, Mich. 49036

[21] Appl. No.: 326,010

[22] Filed: Oct. 19, 1994

[51] Int. Cl.[6] ........................................ A47F 7/00
[52] U.S. Cl. ............................................... 248/129
[58] Field of Search .................... 248/125, 122, 248/129; 280/47.35, 47.34, 304.1; 5/508

[56] References Cited

U.S. PATENT DOCUMENTS

| | | |
|---|---|---|
| 493,811 | 3/1893 | Beckert . |
| 691,270 | 1/1902 | Jones . |
| 956,399 | 4/1910 | Morse . |
| 1,148,980 | 8/1915 | Metaxas . |
| 1,231,654 | 7/1917 | Scher . |
| 1,237,118 | 8/1917 | Stoneham . |
| 1,559,792 | 11/1925 | Seabold . |
| 1,798,565 | 3/1931 | Trullinger . |
| 2,180,042 | 11/1939 | Ettinger . |
| 2,574,743 | 11/1951 | King . |
| 2,675,982 | 4/1954 | Budy . |
| 2,769,482 | 11/1956 | Carlson . |
| 2,843,391 | 7/1958 | Pelletier . |
| 2,991,037 | 7/1961 | Becher, Jr. . |
| 3,396,929 | 8/1968 | Brown . |
| 4,326,731 | 4/1982 | Woychio et al. . |
| 4,332,378 | 6/1982 | Pryor . |
| 4,368,586 | 1/1983 | Forzelias ........................ 248/125 X |
| 4,369,987 | 1/1983 | Witherell . |
| 4,489,454 | 12/1984 | Thompson . |
| 4,718,653 | 1/1988 | Rothman . |
| 4,720,881 | 1/1988 | Meyers . |
| 4,744,536 | 5/1988 | Bancalari . |
| 4,818,135 | 4/1989 | Desjardins . |
| 4,832,294 | 5/1989 | Eidem .............................. 248/129 X |
| 4,844,393 | 7/1989 | Lee . |
| 4,905,944 | 3/1990 | Jost ................................. 248/129 X |
| 4,945,592 | 8/1990 | Sims ................................... 5/508 X |
| 4,977,850 | 12/1990 | King ................................ 248/125 X |
| 4,987,622 | 1/1991 | Shockey . |
| 5,000,407 | 3/1991 | Juji et al. . |
| 5,037,117 | 8/1991 | Hershberger . |
| 5,117,521 | 6/1992 | Foster et al. . |
| 5,135,191 | 8/1992 | Schmuhl . |
| 5,161,764 | 11/1992 | Roney . |
| 5,344,169 | 9/1994 | Pryor ............................ 280/47.35 X |
| 5,396,885 | 3/1995 | Nelson ........................... 248/122 X |
| 5,421,548 | 6/1995 | Bennett .......................... 280/304.1 |

FOREIGN PATENT DOCUMENTS

| | | | |
|---|---|---|---|
| 380875 | 12/1907 | France ............................. 248/125 |
| 447938 | 7/1926 | Germany . | |
| 292850 | 7/1965 | Netherlands . | |
| 1449123 | 1/1989 | U.S.S.R. . | |
| 143440 | 5/1920 | United Kingdom . | |
| 822100 | 10/1959 | United Kingdom ............. 248/122 |
| 1038949 | 8/1966 | United Kingdom . | |
| 2127357 | 4/1984 | United Kingdom . | |

*Primary Examiner*—Ramon O. Ramirez
*Assistant Examiner*—Sarah L. Purol
*Attorney, Agent, or Firm*—Price, Heneveld, Cooper, DeWitt & Litton

[57] ABSTRACT

An intensive care carriage includes a base frame to which poles are mounted. The carriage includes two sections which are detachably interconnected. Each section includes a pole and a base. A platform is mounted on said carriage base frame to support equipment therein. A transducer support is mounted on said pole and permits a transducer attached thereto to permit adjustment of the height of the transducer and to permit the transducer to rotate around the pole.

29 Claims, 3 Drawing Sheets

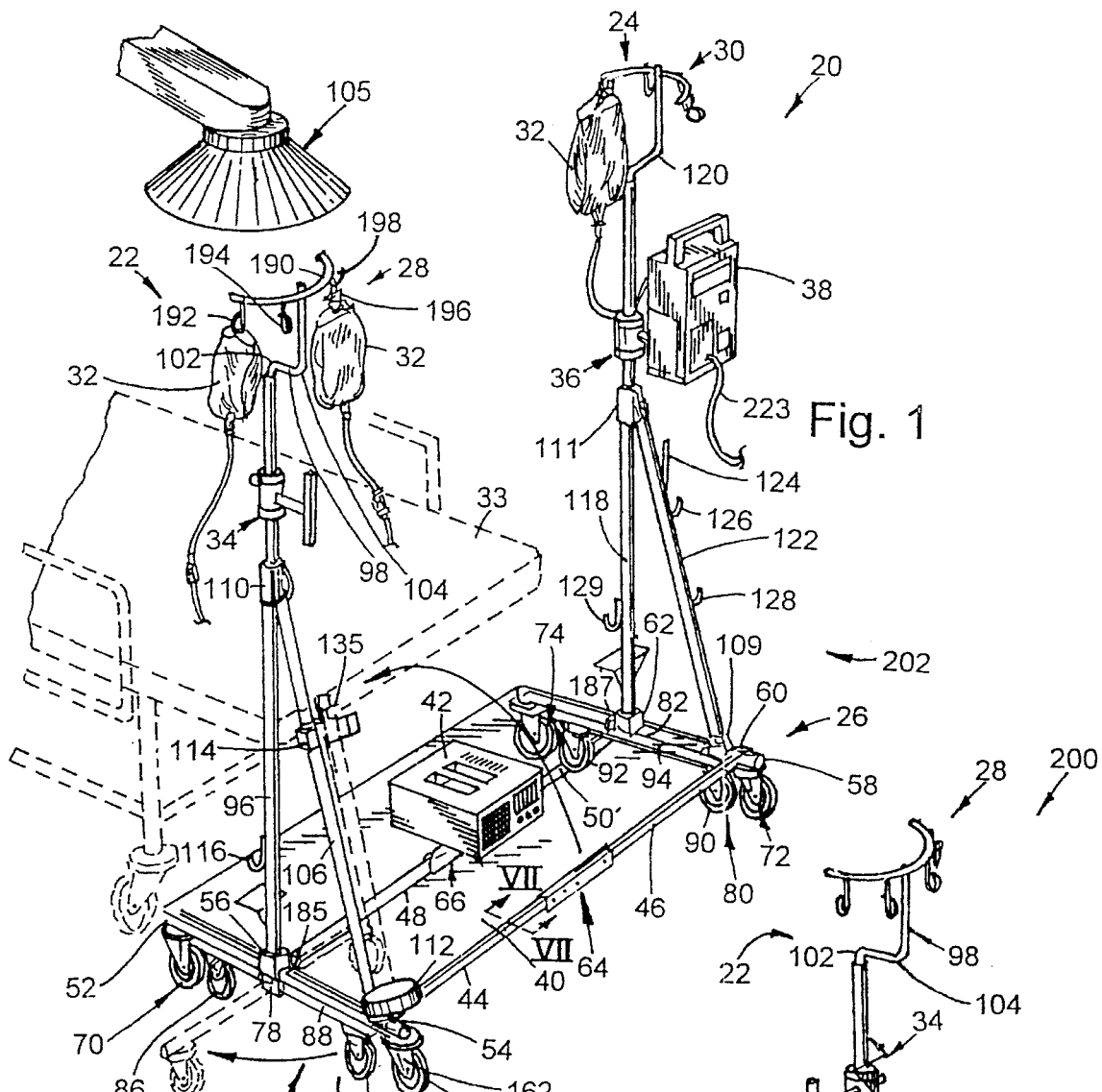
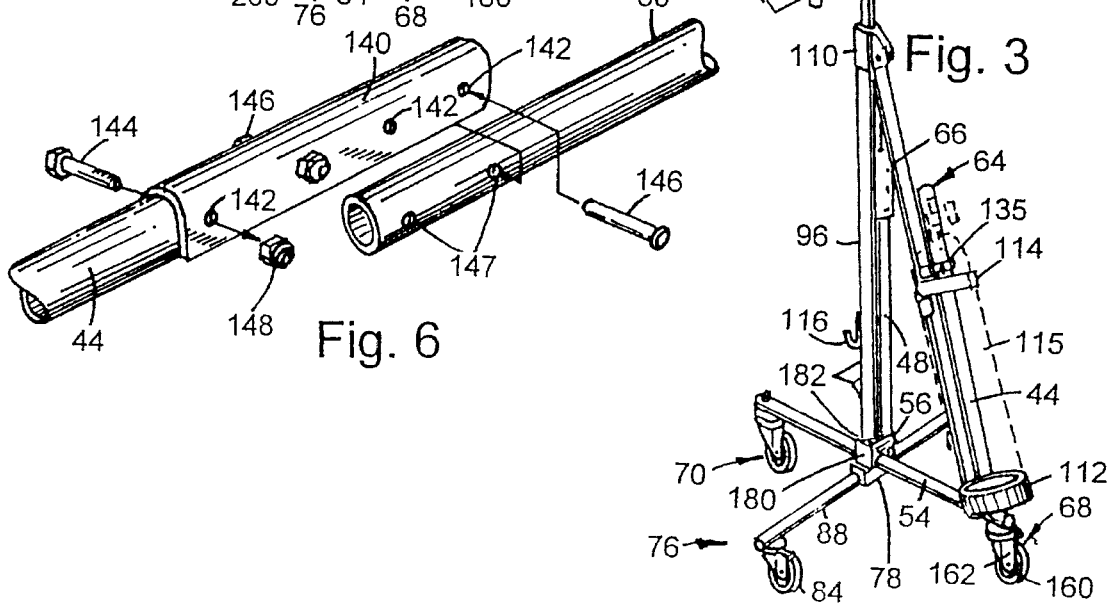

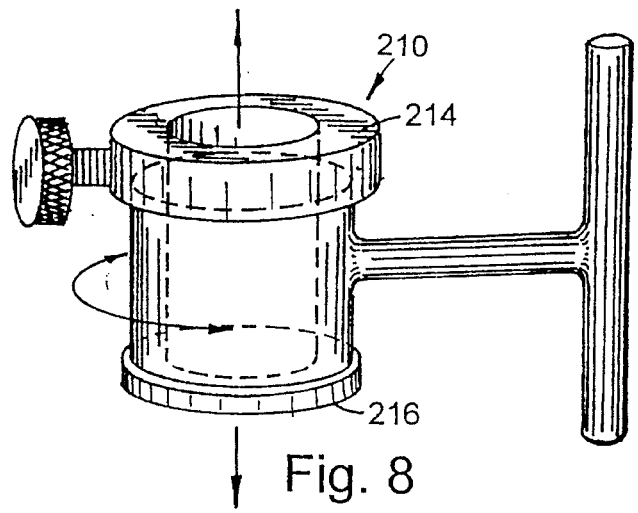
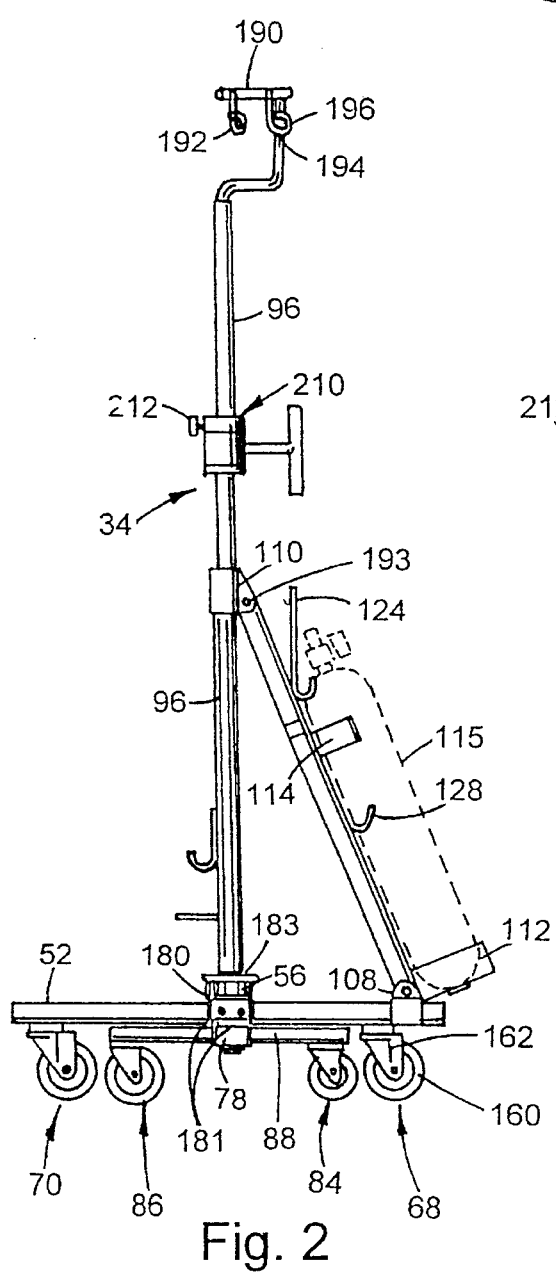
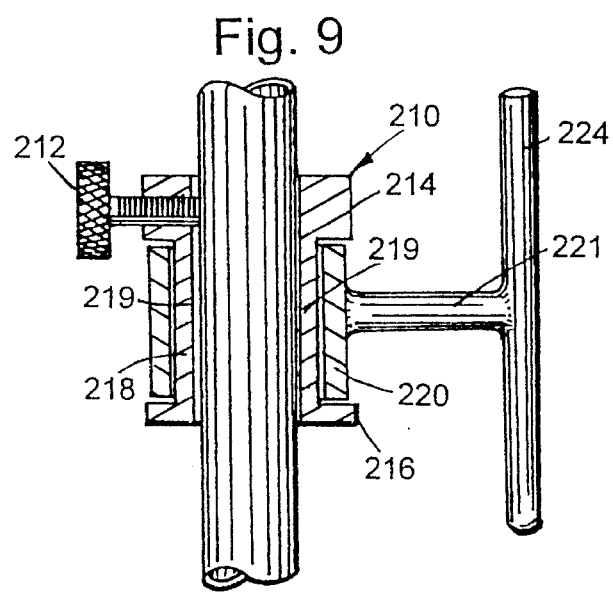
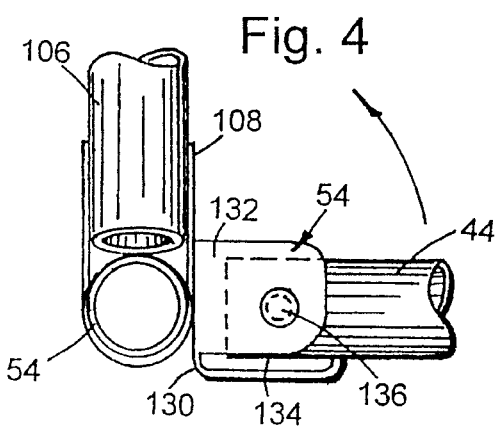

INTENSIVE CARE EQUIPMENT CARRIAGE

BACKGROUND OF THE INVENTION

The present invention pertains to a life support equipment carriage for use with intensive care patients or other critical care patients.

Carriages for life support equipment are well known. These carriages typically include a pole extending upwardly from a base. The pole supports an equipment hanger for IV bags and the like above the patient. The IV bags and transducers are suspended on the equipment hanger or pole, and fluid supply tubes extend from the IV bags and transducers to the patient. The base of the carriage includes wheels on which the carriage rolls to facilitate transport of the equipment with the patient. Such carriages may be interconnected with a hospital bed or gurney, and may include more than one pole.

These carriages are often utilized with intensive care patients who require a wide variety of equipment, including intravenous (IV) bags, transducers, monitors, oxygen tanks, and other devices necessary to sustain and monitor the patient. Such carriages are used with intensive care patients because these patients are typically moved frequently for testing, operations and other treatment. Accordingly, at least a portion of the life support equipment necessary for sustaining and monitoring the patient must be moved with the patient.

A difficulty encountered by attendants, including doctors and nurses, is supporting the equipment in an orderly manner on a number of poles which move independently of one another. In an emergency, hospital personnel must move quickly, since a delay in providing assistance to a patient can result in a more serious injury to the patient. In this volatile environment, independently moving carriages are often moved around to improve attendant access to the patient. Such movement may cause the fluid supply tubes and the electrical cables associated with the equipment supported on the carriages to become entangled. Thereafter, the tubes and cables extending from the equipment supported on the carriages must be untangled before the patient can be moved or equipment can be removed from the carriage. This is particularly problematic if an IV bag must be changed, or if an intensive care patient is to be transported with only a portion of the life support equipment. Thus, an attendant is often required to expend a great deal of time and effort untangling the tubes before the bag can be changed, or the patient transported.

Another difficulty with transducer holders for such carriages is that they do not adequately accommodate movement of the patient. Transducers are typically mounted directly to the carriage pole, and connected to the patient via a fluid supply tube. Movement by the patient creates tension on the supply tube between the transducer and the patient. This tension can disconnect the transducer from the patient, resulting in contamination of the transducer fluid. Additionally, the care provider must be very careful not to create tension on the transducer when moving the patient. This may require that an additional person be present to hold the transducer while the patient is being moved to or from a bed, gurney or surgical table.

Yet another difficulty with existing equipment carriages is the position of devices hung from the equipment hanger associated therewith. Equipment hangers typically have an "X" configuration, wherein each of the four arms supports devices, or an incline configuration, wherein each of the two arms of the hanger supports a device. In either configuration, it is difficult to access all of the arm's of the equipment hangers or to read the labels of bags facing away from the attendant. Even if the attendant places IV bags over one another in order to have the bags on one side, it is difficult to read the labels of, and to replace, the bags hung behind other bags. A further problem encountered with these systems is that the contents of the bags may be contaminated from all the required handling when replacing one or more of the bags hung over one another.

SUMMARY OF THE INVENTION

The present invention overcomes the disadvantages of the prior art devices by providing a more versatile, readily adaptable carriage for life support equipment.

A carriage according to the invention includes first and second sections, each section including a base, a pole extending upwardly from the base and an equipment holder carried on the pole. At least one quick-disconnect connector is associated with each section for detachably connecting the first and second sections, whereby the first and second sections are readily interconnected to form a multiple pole carriage and disconnected to form a plurality of single pole carriages.

According to another aspect of Applicant's invention, the carriage assembly for an intensive care patient includes a base frame assembly. First and second poles are supported on opposite sides of the frame. A planar platform is detachably connected to the base frame and extends between the poles and provides an equipment storage surface.

According to yet another aspect of the invention, a carriage for an intensive care patient includes a base frame with at least one vertical pole supported thereon. Equipment hangers are attached to the pole. Additionally, a transducer holder is supported on the pole. The transducer holder includes a member detachably secured to the pole for adjusting the height of the transducer holder and a moving member rotatingly carried on the holder member for rotational movement thereon. The moving member includes an element to which the transducer is attached.

According to a further aspect of the invention, the equipment hanger includes a generally C-shaped shoulder as viewed from the top, with hangers spaced along the shoulder.

The patient intensive care equipment carriage according to the invention provides a more versatile carriage, facilitating organization of equipment carried thereon which helps the attendants work more efficiently. The carriage allows ready transportation of all, or a portion of, the life support equipment with the patient, and permits easy removal of the equipment supported thereon. Additionally, the equipment hanger presents equipment carried thereon for ready access and high visibility to attendants for a patient.

These and other aspects, features and advantages of the present invention will become apparent upon reading the following detailed description of the preferred embodiments, together with reference to the accompanying drawings, in which:

DESCRIPTION OF THE DRAWINGS

FIG. 1 is a perspective view of a carriage according to the invention with life support equipment supported thereon;

FIG. 2 is a side elevational view of the carriage according to FIG. 1;

FIG. 3 is a perspective view of one section of the carriage according to FIG. 1

FIG. 4 is a fragmentary front elevational view of the carriage of FIG. 1 showing a corner thereof with the joiners rail lowered;

FIG. 6 is an exploded fragmentary perspective view of an interlock mechanism for the carriage according to FIG. 1;

FIG. 8 is a perspective view of a transducer support according to one aspect of the invention; and FIG. 9 is a fragmentary, cross-sectional view of the transducer holder and base post taken along plane IX—IX in FIG. 3.

DETAILED DESCRIPTION OF THE PREFERRED EMBODIMENTS

Figure 7:
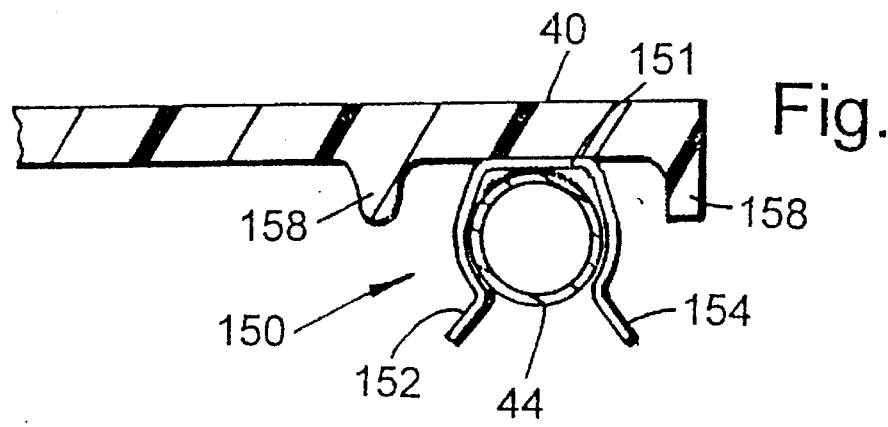
FIG. 7 fragmentary cross-sectional view taken along plane VII-VII in FIG. 1.
Figure 5:
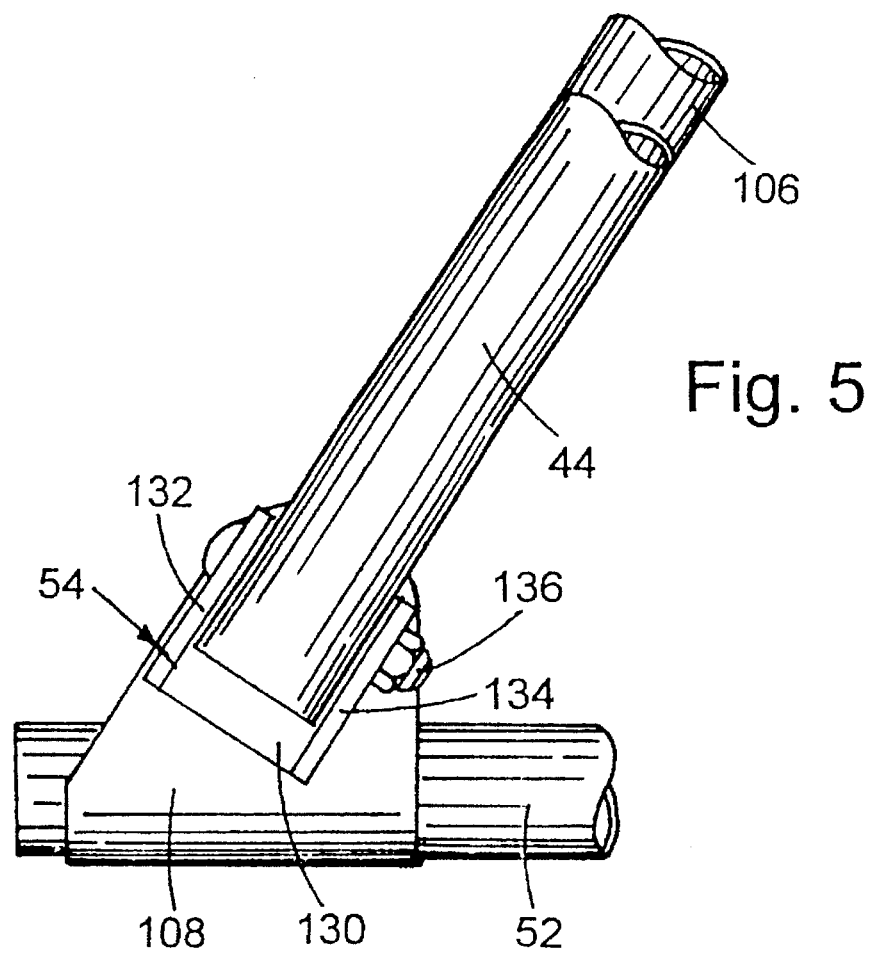
FIG. 5 is a fragmentary, side elevational view of the carriage according to FIG. 1 showing the corner of FIG. 4 with the joiners rail raised.

A patient intensive care equipment carriage 20 according to a preferred embodiment (FIG. 1) includes two vertical pole assemblies 22 and 24 supported on a base frame assembly 26. C-shaped Equipment hangers 28 and 30 are mounted on pole assemblies 22 and 24, respectively, for holding IVs 32, or the like, above a patient (not shown) on a bed or gurney 33 (shown in phantom). Transducer holders 34, 36 are mounted on pole assemblies 22 and 24 for supporting respective transducers such as transducer 38. A platform 40 is mounted on base frame assembly 26 and supports a monitor 42, or other equipment (not shown).

Base frame assembly 26 includes a left front joiner rail 44 and a right front joiner rail 46. A left middle joiner rail 48 and a right middle joiner rail 50 extend in parallel to rails 44 and 46. The left joiner rails 44 and 48 are connected to a side bar 52, by brackets 54 and 56, respectively. Side bar 36 extends orthogonally to the left joiner rails 44, 48. The right joiner rails 46 and 50 are connected to a side bar 58 by brackets 60 and 62, respectively. Side bar 58 extends substantially orthogonally to right joiner rails 46, 50. The front left and right joiner rails 44, 46 are removably interconnected by interlock assembly, or interlock mechanism 64 and the middle left and right joiner rails 48, 50 are removably interconnected by interlock assembly 66. Wheel assemblies 68 and 70 are attached to opposite ends of side bar 52. Wheel assemblies 72 and 74 are mounted at opposite ends of side bar 58. A wheel is thus employed at each corner of the base frame assembly to provide a stable transport means for the carriage 20. The joiner rails each have a length of approximately fifteen inches and the side bars each have a length of approximately eighteen inches. The bracket 56 is positioned at the center of side bar 52.

The base frame assembly also includes a chassis 76 pivotally mounted to side bar 52 by a bracket 78 and a chassis 80 pivotally mounted to side bar 58 by a bracket 82. Chassis 76 includes a wheel assembly 84 and a wheel assembly 86 on opposite ends of an arm 88. Chassis 80 includes a wheel assembly 90 and a wheel assembly 92 on opposite ends of an arm 94.

Pole assembly 22 includes a base post 96 supported in bracket 56. An elbow 98 is received in the top of base post 96. Hanger assembly 28 includes a shoulder 190 mounted to elbow 98. Elbow 98 includes bends 100 and 102 which space shoulder 190 from the longitudinal axis of base plate 96. The distance between bends 100 and 102 is approximately four inches. The distance from shoulder 190 to bend 102 is approximately eight inches. The offset of the shoulder from the pole is preferably away from the patient (toward the front of the carriage). This facilitates the anesthesiologist's access to equipment hung on the hangers 28, 30, thereby decreasing the risk of contamination due to mishandling, and moves the hangers away from the rotating overhead surgical light 105.

Transducer support 34 is attached to base post 96, as described in greater detail hereinbelow. A support member 106 is connected to side bar 52 by a bracket 108 (FIG. 3) and to base post 96 by post bracket 110. Bracket 110 is approximately thirty inches above bracket 56. The support member 106 increases the load which the pole assembly 22 can support. An oxygen tank holder including a platter 112 and a U-shaped support 114 is mounted on support member 106 to support an oxygen tank 115 (shown in phantom in FIG. 2). A hook 116 is attached to base post 96 for holding an infusion pump, or the like.

The pole assembly 24 is substantially identical to pole assembly including a base post 118, an elbow 120 and a support member 122. A post 124 and hooks 126 and 128 are mounted on support member 122. Post 124 is for holding a cardiac bucket (not shown), which may, for example, have ice therein. Hooks 126, 128 and 129 are provided to hold other equipment, such as CO fluid, pumps, or the like.

The joiner rails 44, 46, 48, 50, side bars 52, 58, arms 88, base posts 96, 118 and supports 106, 122 are preferably manufactured from a suitable lightweight, yet strong tubing, and may for example be constructed of stainless steel or an aluminum alloy, or an other suitable metal tubing manufactured by a conventional process. Those skilled in the art will recognize that other materials may be used which are strong or strong and lightweight, and may be solid or tubular construction.

The left front joiner rail 44 is connected to bracket 108 (FIGS. 3 and 4) which is attached to side bar 52 by U-shaped joiner bracket 54. Brackets 54 and 108 are preferably stainless steel, and may be manufactured by any suitable means such as by stamping. The bracket includes a base 130 attached to corner bracket 108 by any suitable conventional means such as welding, rivets, threaded fasteners, or the like. The joiner bracket 54 also includes arms 132 and 134 projecting orthogonally from base 130. An axle 136 extends through arms 132 and joiner rail 134. The axle may be implemented using a bolt 131 and lock bolt 133, or any other suitable means. Joiner rail 44 is mounted on axle 136 such that it pivots between a lowered position (FIG. 1) and a raised position (FIG. 3) abutting with support member 106. A resilient clip 135, or the like, attached to support member 106, and may be provided to receive joiner rail 44 to secure joiner rail 44 is in the raised position. Bracket 60 is connected to side bar 58 via a bracket 109, and brackets 60 and 109 are identical to brackets 54 and 108, respectively, and therefore will not be described in greater detail hereinbelow.

Interlock assembly 64 includes an elongated member 140 having a U-shaped cross-section and an interior radius which is approximately equal to the outer radius of joiner rails 44 and 46, such that member 140 fits snugly over the joiner members. Member 140 may be manufactured of any suitable metal, such as aluminum, stainless steel, or the like, or a strong plastic. Member 140 includes four apertures 142 for receipt of fasteners 144, 146. When member 140 is positioned over rail 44, and apertures 147 are aligned with apertures 142, bolts 144 are inserted through apertures 142, 147 and nuts 148 are attached to bolts 144. This secures member 140 to rail 44. Member 140 may alternately be fixedly attached to joinder member 44 by welding, rivets, or the like. Member 140 thus moves with joinder member 44. Member 140 is detachably connected to joinder rail 46 by a quick-disconnect connector, or lock element, such as pin 146. Pin 146 may include any suitable lock mechanism such as a ball joint and spring sleeve, a cotter pin, elongated fastener head and slot, or the like (not shown). The pins 146 are secured in member 140 and joinder 50 by the removable lock mechanism (not shown). Interlock assembly 66 is identical to assembly 64 and accordingly, is not described in greater detail herein. Platform 40 (FIG. 1) is carried on base frame assembly 26. Platform 40 is rectangular, and is removably secured to the side bars and front bars by a plurality of U-shaped clips 150 (FIG. 7, only one of which is shown). The U-clips 150 each include a base 151 connected to the platform 40 by rivets, threaded fasteners, welding or the like. The U-shaped clips also include resilient arms 152, 154 which releasably engage the joinder bars 44, 46, 48 and 50 and side bars 52, 54. In the preferred embodiment, two clips 150 are attached to each of the side bars 52, 58 and at least one clip 150 is attached to each of the joinder rails 44, 46, 48 and 50. Platform 40 is constructed of a suitable material, such as a honeycomb polymer platform or a solid, thin, planar polymeric member including ribs 158. When the platform is attached to the side rails and joinder rails, the platform provides stability against twisting of the side bars 52, 58 relative to joinder rails 44, 46, 48, 50. Platform 40 is light in weight and strong enough to support oxygen tank 115, monitor 42, and the like. Additional support for the platform 40 is provided by central joinder members 48, 50. The readily detachable platform is particularly advantageous in an operating room to increase access to the operating cable and pedals (not shown).

The wheel assemblies 68 (FIG. 1) 70, 72, 74, 84, 86, 90 and 92 are substantially identical. Accordingly, only wheel assembly 68 is described in greater detail herein. Wheel assembly 68 includes a wheel 160 supported on a fork 162. Fork 162 is attached to side bar 52 by a suitable, conventional swivel joint connector. The fork rotates at least 90 degrees, and most preferably, freely rotates 360 degrees in a horizontal plane. The rotation of the fork permits the carriage to be transported in any direction from a standstill, thereby facilitating free movement of the carriage in any direction. The wheel assemblies 84, 86, 90 and 92 are preferably smaller in height (see FIG. 2) than wheel assemblies 68, 70, 72 and 74 to permit the chassis 76, 80 to be pivoted below the side bar 54, 58.

Bracket 78 is connected to bracket 56 by a conventional swivel joint, or the like, which releasably locks at a first position parallel to bar 52 (FIG. 1) and locks at a transverse position orthogonal to bar 52 (FIG. 3). In each position, the lock is preferably easily released to pivot the chassis 76 and 80 to the other position. For example, the lock may include a resilient member, such as a latch (not shown) attached to bracket 78 and releasably engaging complementary members (not shown) on bracket 56 when arm 88 is parallel to bar 52 and when arm 88 is transverse to bar 52. However, any suitable releasable lock mechanism could be utilized.

Bracket 56 includes a generally rectangular block 180 (FIGS. 2 and 3) having a cylindrical aperture for snug receipt of side bar 52. Side bar 52 is fixedly secured against rotation relative to block 180 by welding, threaded fasteners 181 (FIG. 2), or the like. Block 180 also includes a cylindrical recess 182 (FIG. 3) in the top thereof for snug receipt of post 96. Post 96 is secured in recess, or counterbore, 182 by welding, a fastener 183, or the like. The block may be manufactured from any suitable material such as aluminum, stainless steel, or the like. Joinder rail 48 is attached to block 180 by a bracket 185 (FIG. 1) identical to bracket 54 and joinder rail 50 is connected to block 62 by a bracket 187 identical to bracket 185. Accordingly, brackets 185 and 187 will not be described in greater detail hereinbelow. However, it is noted that the axle of brackets 54, 60, 185 and 187 must be oriented orthogonally to the longitudinal center line of support member 106 and base post 96 for the joinder rails 44 and 48 to pivot to a position against and aligned with the support member 106 and base post 96, respectively.

Hanger assembly 28 includes a metal, C-shaped shoulder 190 welded, or otherwise attached, to elbow 98. Four hooks 192, 194, 196 and 198 are mounted on shoulder 190. The hooks are attached to the C-shaped shoulder by any suitable means such as welding, fasteners, or the like. The shoulder and hooks are of any suitable material such as stainless steel, an aluminum alloy, or the like. The C-shaped shoulder positions the hooks such that IV bags hung therefrom face outwardly and do not overlap. The bags face the attendant from the front and side of the carriage making it easier to read the bags. Additionally, devices hung from hanger assembly 28 are readily accessible to the attendant from the side and front of the carriage (e.g., the anesthesiologist is positioned at, or near, the patient's head and has easy access to the front and side of the carriage). The fact that the bags are more readily accessible decreases the risk of contamination by avoiding mishandling of the bags and eliminating the need to hang bags over other bags.

The support member 106 (FIG. 2) is attached to base post 96 by pole bracket 110. Pole bracket 10 is attached to base post 96 by welding, threaded fastener, rivets, or the like. The support member 06 is attached to bracket 110 by welding, a rivet, a threaded fastener 193, or the like. The support member 106 provides additional rigidity to the carriage poles. The support member faces the anesthesiologist's side (front) of the carriage so the back half of the carriage may be positioned under the overhang of bed 33 (FIG. 1). This is particularly helpful where a bed includes foot pedals (not shown) or other components which are positioned near the floor the carriage side bars 52, 58 will not interfere with the operation of such components.

The patient intensive care equipment carriage 20 (FIG. 1) is separable into two sections 200 and 202. Sections 200 and 202 are substantially identical, although complimentary. Section 200 is shown in FIG. 3. Section 200 includes pole assembly 22. When disconnected from section 202, chassis 76 is pivoted outwardly to the transverse position to provide a stable base for pole assembly 22. Sections 200 and 202 are connected by interlock assemblies 64 and 66, such that joinders 44, 46, 48 and 50 are readily detached and reassembled. This allows the equipment carriage 20 to be readily broken down for transporting only one of the pole assemblies 22, 24 with the patient. The sections are readily reassembled using the connection assemblies 64 and 66. The interconnected assemblies provide a rigid structure with fixedly spaced pole assemblies 22, 24 for ease of use and preventing relative movement of the two poles, thereby reducing entangling of the equipment hung on the poles.

Transducer holder 34 (FIGS. 2, 8 and 9) includes a collar 210 which is secured to base post 96 using a threaded pin 212. The collar 210 includes a top flange 214 and a bottom flange 216. A central cylinder 218 extends between the top and bottom flanges. An outer cylinder 220 is movably supported on collar 210 between the flanges 214 and 216 for free rotation around the central cylinder region 218. Collar 210 may have a two-piece construction which is interconnected with cylinder 220 positioned over cylinder 218. Weldmont 219, snap connectors, or the like, may be used to connect the pieces of collar 210. An arm 221 extends orthogonally outwardly from cylinder region 220. Arm 221 may be welded, or otherwise secured, to cylinder 220, and has a length of approximately four inches. A shaft 224 is mounted to a distal end of arm 221 opposite the end welded to cylinder 220. The components of the transducer support are preferably manufactured of a strong metal such as an aluminum alloy, stainless steel, or a rigid polymer, or other durable material. Transducer holder 36 is identical to transducer holder 34.

The height of transducer holder 36 is adjustable to move the transducer 38 to a height appropriate for the patient. The rotating member 220 of transducer holder 36 allows transducer 38 to move with movement of IV line 223. Such movement can occur when the patient moves in the bed or when the patient is moved between a bed and a gurney. The transducer will thus rotate to a position which minimizes the tension on IV tube 223, thereby decreasing the chance that IV 223 will be separated from transducer 38 the risk of IV contamination.

It is envisioned that each hook 116, 124, 126, 128 and 129 will have a label identifying the equipment to be supported thereon. This standardizes pole utilization between the operating room, intensive care unit, etc. As a consequence, the organization of the carriage equipment will be enhanced.

To assemble the patient intensive carriage, brackets 54 and 60 are connected to the side rails 52 and 58 via brackets 108 and 109. Side bars 52 and 58 are received in brackets 56 and 62, and secured thereto. Joinder bars 48 and 50 are pivotally secured to brackets 185 and 187 after these brackets are secured to brackets 56 and 62, respectively. The wheel assemblies 68, 70, 72, 74, 84, 86, 90, 92 are mounted to side bars 52, 58 and arms 88, 94 by conventional pivot connections. The wheel assemblies 68, 70, 72, 74 are secured to the side bars 52, 58 by inserting respective pins associated with each wheel assembly into a bar and securing them therein using a retaining clip or other suitable securing method. Bracket 78 is attached to bracket 56 and bracket 82 is attached to bracket 62. Base posts 96 and 118 are inserted into the vertical pole mounting brackets 56 and 62, respectively, and secured thereto by welding, threaded fastener, or the like. The chassis brackets 78 and 82 are then secured to the brackets 56 and 62 by a respective pivot and lock mechanism. The locking assembly member 140 is then secured to the joinder rail 44 using threaded bolts 144 and nuts 148. The locking assembly member 140 is secured to joinder rail 50 by locking pin 146.

Brackets 108 and 109 are secured to sidecars 52 and 58 and brackets 110 and 111 are secured to base posts 96 and 118 with support members 106 and 122 extending therebetween. Platform 40 is assembled to the joinder rails 44, 46, 48 and 50 and side bars 52, 58 using clips 150.

The oxygen tank holder components 112, 114 and hooks 116, 129, 126, 128 and post 124 are welded to the base posts 96, 118 and support members 106, 122. The transducer support is secured to base post 98 by sliding it thereon and locking it into position using the lock pin 212. The shoulder 190 is attached to elbow 98. The elbows 98 and 120 are secured to the top of the base posts 96, 118 by welding, threaded fastener, or the like.

In use, the base post is adjustable to vary the height of the holder 28. The elbow may be vertically slidable to adjust the height of the holder 28. This height adjustment may be provided by any suitable lock mechanism. Additionally, pin 212 releasably engages base post 96 to slidably adjust the height of the transducer holder assembly 54. The pins 146 are inserted into, and removed from, engagement member 140 and side bar 50 to permit the folding of the joinder rails 44 and 46 between a raised position (FIG. 3) and a lowered position (FIG. 1). A latch (not shown) may be provided to secure joinder rail 44 to support member 106. The platform 40 is removed by disengaging clamps from the joinder rails 44, 46, 48, 50 and side bars 52, 58.

Accordingly, it can be seen that a carriage 20 for use with intensive care patients is disclosed. The carriage is more versatile in use than heretofore known carriages, allowing the ready disassembly and reassembly of the carriage into a single multiple pole unit or multiple single pole units. This facilitates orderly use of the assembled units 200, 202, and the ready removal and movement of the life support systems, and the separation of units 200, 202 to transport a portion of the equipment. The spacing of the base posts 96, 118 from the back wheel assemblies 70, 74 permits the base frame assembly to be slid below the end of bed 33, as shown in FIG. 1, such that the base frame is partially tucked out of the way of attendants in use.

It is to be understood that the foregoing description of the preferred embodiments of the invention is provided for purposes of description and illustration, and not as a measure of the invention, whose scope is to be defined by reference to the ensuing claims. Thus, those skilled in the art may devise embodiments of the particular concepts presented in the foregoing illustrative disclosure which differ from the particular embodiments shown and described in detail herein, or may make various changes in the structural details of the illustrated embodiments. For example, continuous tubes may be substituted for the joinder rails and interlock mechanisms, and the chassis may be omitted, to provide a multiple pole carriage which does not separate into multiple single pole carriages. Accordingly, all alternative or modified embodiments which utilize the underlying concepts of the invention, and incorporate the spirit thereof, are to be considered as within the scope of the claims appended hereinbelow unless such claims, by their language, specifically state otherwise.

The embodiments of the invention in which an exclusive property or privilege is claimed are defined as follows:

1. A carriage for an intensive care patient, comprising:
   first and second sections, each section including a base, a pole extending upwardly from said base;
   at least one equipment carried on at least one of said first and second section poles;
   at least one quick-disconnect connector detachably connecting said first and second sections, whereby said first and second sections are interconnected to form a multiple pole carriage and disconnected to form a plurality of single pole carriages.

2. The carriage assembly as defined in claim 1, wherein said first and second sections each include a joinder rail, and said joinder rails of said first and second sections are detachably interconnected by said quick-disconnect connecter.

3. The carriage assembly as defined in claim 2, wherein said quick-disconnect connector includes a member fixedly carried on one of said first and second section joinder rails and a mechanism for detachably securing said member to the other one of said first and second section joinder rails.

4. The carriage assembly as defined in claim 3, wherein said mechanism includes a pin.

5. The carriage assembly as defined in claim 2, wherein said first and second section bases each include a side bar and said first and second joinder rails is assembled to said first and second section side bars, respectively.

6. The carriage assembly as defined in claim 5, wherein said first and second section poles are carried on said side bar and further including a support member extending between each said side bar and each said pole.

7. The carriage assembly as defined in claim 6, whereby said first and second section joinder rails are pivotably attached to said first and second section side bars, respectively, to pivot between a lowered position and a raised position, said first and second section side bars abutting against said first and second section support members, respectively, when in said raised position.

8. The carriage as defined in claim 1, further including connectors, a platform detachably connecting said platform to said first and second section joinder rails and said side bars.

9. The carriage assembly as defined in claim 1, further including a transducer holder supported on said pole, said transducer holder including a fixed member detachably secured to said pole whereby the height of said fixed member is adjusted and a moving member carried on said fixed member to rotate on said fixed member, said moving member including an engagement element for receiving the transducer, such that a transducer carried on said moving member rotates horizontally on said pole.

10. The carriage as defined in claim 1, wherein each of said first and second sections includes a chassis, said chassis including an arm and at least one wheel, and a connector pivotably connecting said first and second section arms to said first and second section side bars, whereby said arm moves pivotally between a position parallel to said side bar and a position orthogonal to said side bar.

11. The carriage as defined in claim 10, wherein said first and second section chassis each include two wheels carried on opposite ends of said arm.

12. The carriage as defined in claim 1, wherein said at least one equipment hanger includes an elbow connected to said at least one first and second section pole and a shoulder connected to said elbow.

13. The carriage as defined in claim 12, wherein said elbow spaces said shoulder laterally from the longitudinal axis of said at least one of said first and second poles.

14. The carriage assembly as defined in claim 12, wherein said shoulder is generally C-shaped, and further including hooks attached to said C-shaped holder.

15. A carriage assembly for an intensive care patient, comprising:
a base frame assembly;
a planar platform; and
at least one vertically extending pole supported on said frame on opposite sides of said platform; and
connectors for releasably connecting said platform to said frame, whereby said platform provides a horizontal surface for equipment storage and said platform is readily disconnected from the base frame.

16. The carriage assembly as defined in claim 15, wherein said base includes a generally rectangular planar surface and ribs extending orthogonally thereto.

17. The carriage assembly as defined in claim 15, wherein said base frame includes side rails, joinder rails, and mounting brackets interconnecting the side rails and joinder rails.

18. The carriage assembly as defined in claim 15, wherein said platform is generally rectangular and said connectors include clips releasably engaging said frame.

19. The carriage assembly as defined in claim 15, further including a transducer holder supported on said pole, said transducer holder including a fixed member detachably secured to said pole whereby the height of said fixed member and a moving member carried on said fixed member to rotate on said fixed member, said moving member including an engagement element for receiving the transducer, such that a transducer carried on said moving member rotates horizontally on said pole.

20. The carriage as defined in claim 15, wherein said at least one equipment hanger includes an elbow connected to said at least one first and second section pole and a shoulder connected to said elbow.

21. The carriage as defined in claim 20, wherein said elbow spaces said shoulder laterally from the longitudinal axis of said at least one of said first and second poles.

22. The carriage assembly as defined in claim 21, wherein said shoulder is generally C-shaped, and further including hooks attached to said C-shaped shoulder.

23. A carriage assembly for an intensive care patient comprising:
a base frame assembly;
at least one pole supported on said base frame;
an equipment hanger attached to said at least one pole; and
a transducer holder supported on said at least one pole, said transducer holder including a support member detachably secured to said at least one pole to adjust the height of said transducer holder on said at least one pole, and a moving member carried on said support member for rotational movement around said support member, said moving member including an engagement element receiving the transducer such that said transducer rotates horizontally on said at least one pole, said support member including a cylinder and at least one flange.

24. The carriage assembly as defined in claim 23, wherein said cylinder is positioned around said at least one pole and releasably secured to said at least one pole by a lock mechanism.

25. The carriage assembly as defined in claim 24, wherein said lock mechanism includes a threaded fastener extending through said support member and engaging said at least one pole to secure the transducer at a selected height.

26. The carriage as defined in claim 23, wherein said at least one equipment hanger includes an elbow connected to said at least one pole and a shoulder connected to said elbow.

27. The carriage as defined in claim 26, wherein said elbow spaces said shoulder laterally from the longitudinal axis of said at least one pole.

28. The carriage assembly as defined in claim 28, wherein said shoulder is generally C-shaped, and further including hooks attached to said C-shaped shoulder.

29. A carriage assembly for a patient, comprising:
a base frame;
at least one pole extending upwardly from said base frame;
an equipment hanger including a generally C-shaped shoulder coupled to said pole and extending in a horizontal plane, and a plurality of hooks mounted to said shoulder and spaced along said shoulder; and
an elbow extending between said shoulder and said pole, said elbow spacing said shoulder from the longitudinal axis of said pole.

* * * * *